United States Patent [19]
Johnson et al.

[11] Patent Number: 5,622,589
[45] Date of Patent: Apr. 22, 1997

[54] METHOD FOR MAKING A FLANGELESS SEAM FOR USE IN DISPOSABLE ARTICLES

[75] Inventors: Larry K. Johnson, Pleasant Plain; Stephen J. Lange, Cincinnati, both of Ohio

[73] Assignee: The Procter & Gamble Company, Cincinnati, Ohio

[21] Appl. No.: 541,996

[22] Filed: Oct. 10, 1995

[51] Int. Cl.⁶ .............................. B32B 31/00; A61F 13/15
[52] U.S. Cl. ..................... 156/289; 156/308.4; 604/385.1
[58] Field of Search ........................ 2/236, 237; 156/159, 156/216, 217, 218, 227, 203, 251, 254, 289, 308.4, 157; 604/385.1, 385.2, 390

[56] References Cited

U.S. PATENT DOCUMENTS

| | | | |
|---|---|---|---|
| 2,298,522 | 10/1942 | Waters | 93/35 |
| 2,494,905 | 1/1950 | Shumann | 93/35 |
| 4,610,681 | 9/1986 | Strohbeen et al. | 604/396 |
| 4,731,070 | 3/1988 | Koci | 604/385 R |
| 4,890,763 | 1/1990 | Curiel | 220/455 |
| 4,938,753 | 7/1990 | Van Gompel et al. | 604/385.2 |
| 5,185,052 | 2/1993 | Chappell et al. | 156/462 |
| 5,236,430 | 8/1993 | Bridges | 604/396 |
| 5,246,433 | 9/1993 | Hasse et al. | 604/396 |

*Primary Examiner*—David A. Simmons
*Assistant Examiner*—Jerry Allen Lorengo
*Attorney, Agent, or Firm*—David M. Weirich; Steven W. Miller; Jacobus C. Rasser

[57] ABSTRACT

According to the present invention, a method of making flangeless seams especially useful in disposable articles, such as training pants, incontinence articles and the like is provided. The method includes the steps of: (1) providing a first member of the disposable article; (2) providing a barrier member; (3) folding the first member of the disposable article about the barrier member providing opposing proximal and distal portions of the first member, the barrier member being disposed at least partially between the opposing proximal and distal portions; (4) providing a second member of the disposable article juxtaposed at least a portion of the first member to form a laminate including the first member, the second member and the barrier member; and (5) applying a joining means across at least a portion of laminate, the joining means joining at least a portion of the first member and the second member, the barrier member preventing the joining means from joining the proximal portion with the distal portion.

19 Claims, 6 Drawing Sheets

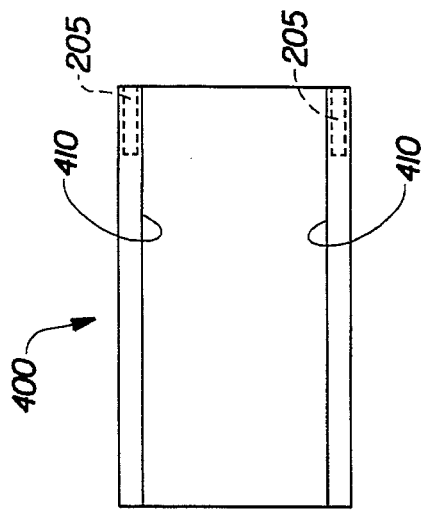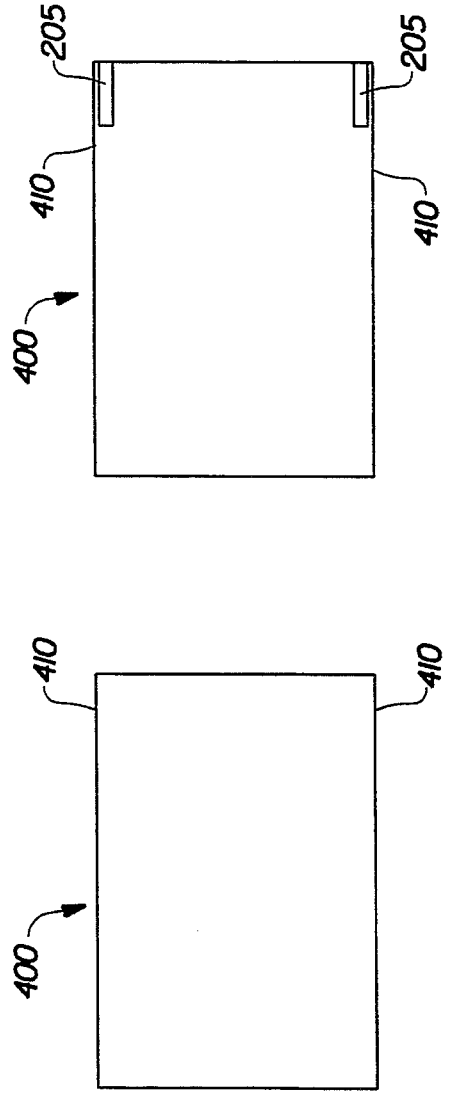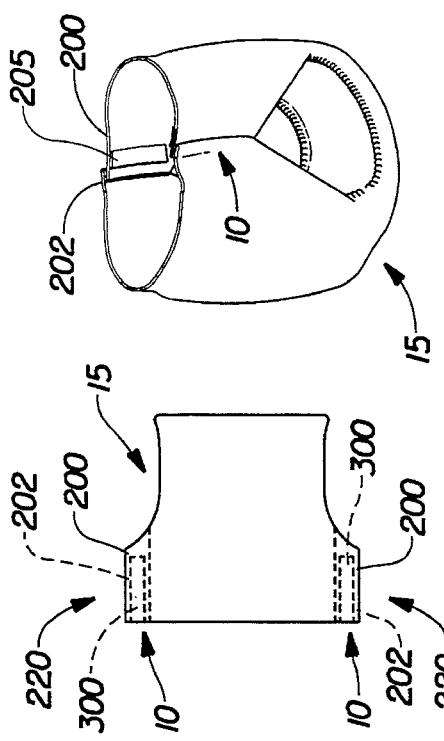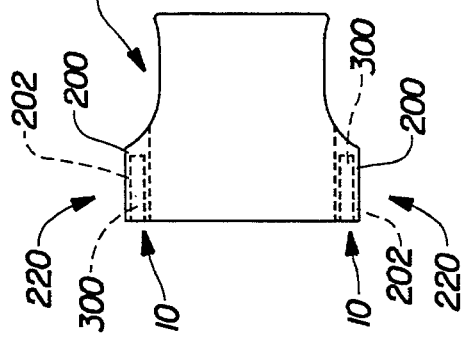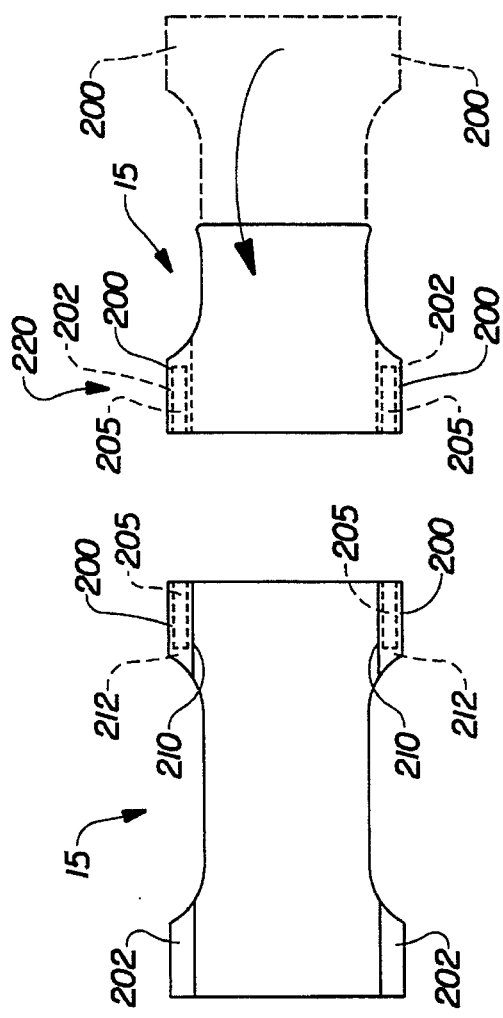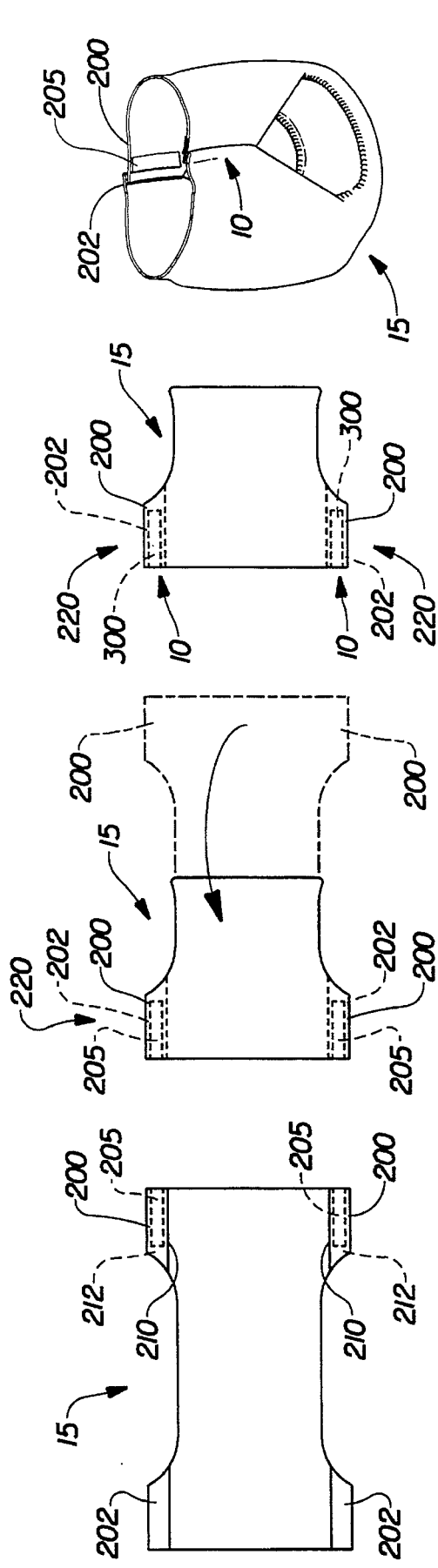

METHOD FOR MAKING A FLANGELESS SEAM FOR USE IN DISPOSABLE ARTICLES

FIELD OF THE INVENTION

The present invention relates to a method for making flangeless seams especially preferred for use in disposable, pant-like articles having at least one fixed side comprising a seam. Examples of such disposable articles include training pants, pull-on diapers or adult incontinence articles, disposable underwear for children (e.g., toddlers) or adults, and disposable panties which may be used with catamenial devices such as tampons or sanitary napkins.

BACKGROUND OF THE INVENTION

Infants and other incontinent individuals wear disposable absorbent articles to receive and contain urine and other bodily exudates. Absorbent articles having fixed sides have been popular for use in adult incontinence articles and children's toilet-training articles because it is desirable to have an absorbent article which is very garment-like in appearance and feel. (As used herein, "articles having fixed sides" refer to disposable articles such as adult incontinence briefs and training pants which are provided to the consumer in a pant-like configuration. Thus, the articles generally have the front and rear portions joined together to form a waist hoop and leg holes. This is unlike conventional diapers which are provided to the consumer with the front and rear portions unjoined.) For adults, the garment-like appearance and feel can help reduce any embarrassment associated with the use of incontinence articles. For children, especially in their toilet training stage, the garment-like feel and appearance can help the child distinguish the article, such as training pants, from a diaper and can help the child adjust to cloth undergarments.

With regard to disposable articles such as adult incontinence briefs and training pants, consumers are very conscious about the fit, containment characteristics and the overall appearance of the articles. One improvement that has become popular with consumers has been the addition of stretch or elasticity throughout different portions of the articles. One example of a commercially available disposable training pant is disclosed in U.S. Pat. No. 5,246,433 entitled "Elasticized Disposable Training Pant and Method of Making the Same", issued to Hasse et al. on Sep. 21, 1993.

Despite the improvements made to disposable articles having fixed sides, such articles generally include seams for joining the front and rear portions. The seams are often constructed by positioning the lateral edges of the front and rear portions of the article in a face-to-face relationship with one another and then gluing, sewing, heat sealing, pressure bonding or ultrasonically sealing the edges to form flanges or fin seams. Flanges or fin seams can be unsightly if located on the outwardly facing surface of the article or irritating to the wearer if located on the inward surface. Thus, attempts have been made to reduce the outwardly or inwardly extending portions of the flanges of fin seams. However, doing so may reduce the strength of the bond between the front and rear portions of the article which may allow the seam to fail during use.

Another important aspect of a disposable article is the cost of the article. Because the article is intended to be discarded, generally after a single use, consumers are very conscious of the cost of the article. Thus, it would be advantageous to be able to provide a seam that can be constructed economically on machinery that is very similar to that already in place. Further, it would be advantageous to reduce the amount of material that is needed to produce a satisfactory seam or that is wasted in attempting to make the seam preferable to the consumer.

Therefore, it is an object of the present invention to provide a method of making flangeless seams especially suited for use in disposable articles, such as disposable training pants, adult incontinence briefs and the like which are discrete, strong and economical to manufacture.

It is another object of the present invention to provide a method of making flangeless side seams which can be produced more quickly and easily than the sewn seams of the prior art and which provide a more garment-like appearance and are less irritating than the heat-sealed, adhesively bonded or ultrasonically sealed seams of the prior art.

It is yet another object of the present invention to provide a method of making flangeless side seams which reduces the amount of material needed to produce the seam as well as the material waste associated with providing a seam that is acceptable to the consumer.

It is still another object of the present invention to provide a method for manufacturing a flangeless seam for use with disposable articles that can be made on the machinery used to make currently available flange, fin or butt seams with minor modifications.

It is a further object of the present invention to provide a disposable article, such as disposable training pants, having flangeless seams.

SUMMARY OF THE INVENTION

According to the present invention, a method of making flangeless seams especially useful in disposable articles, such as training pants, incontinence articles and the like is provided. The method includes the steps of: (1) providing a first member of the disposable article; (2) providing a barrier member; (3) folding the first member of the disposable article about the barrier member providing opposing proximal and distal portions of the first member, the barrier member being disposed at least partially between the opposing proximal and distal portions; (4) providing a second member of the disposable article juxtaposed at least a portion of the first member to form a laminate including the first member, the second member and the barrier member; and (5) applying a joining means across at least a portion of laminate, the joining means joining at least a portion of the first member and the second member, the barrier member preventing the joining means from joining the proximal portion with the distal portion.

While the seams made by the method of the present invention may be used in any disposable article, a preferred disposable article comprises an elasticized waistband, elasticized leg cuffs and an absorbent assembly comprising a backsheet, topsheet, and absorbent core.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

FIGS. 9A–G show a schematic view of a portion of one preferred embodiment of the method of the present invention.

DETAILED DESCRIPTION OF THE INVENTION

Figure 1:
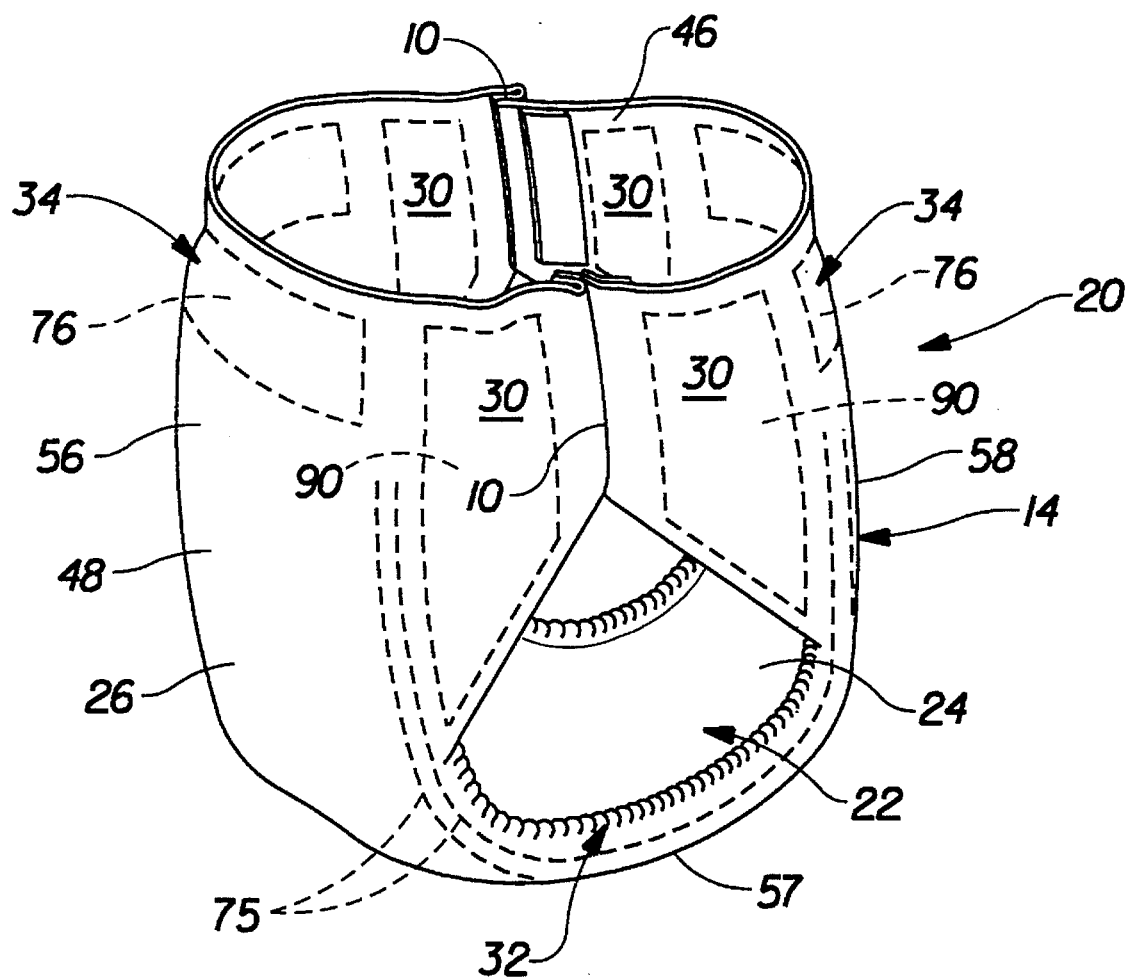
FIG. 1 is a perspective view of one embodiment of a disposal training pant in a typical in-use configuration as it would be applied to a wearer comprising a seam formed by one embodiment of the present invention.

Referring to the drawings, it will be noted that FIG. 1 is a perspective view of a unitary disposable article. A unitary disposable article is one which is intended to be discarded after it is used (i.e., it is not intended to be laundered or otherwise restored or reused). The disposable article may be provided with an absorbent assembly which is placed in close proximity to the body of the wearer to absorb and contain the various exudates discharged from the body. A preferred embodiment of the disposable article of the present invention, disposable training pants 20, is shown in FIG. 1.

The training pants 20 of FIG. 1, preferably comprise a chassis 14, an absorbent assembly 22, and at least one flangeless seam 10. (As used herein the term "flangeless seam" refers to a seam which extends from the disposable training pants 20 about ⅛ inch or less. Preferably the flangeless seam 10 will extend from the article about 1/16 inch or less, and more preferably 1/32 inch or less.) The chassis 14 of the present invention preferably has a symmetric, modified hour-glass shape. The chassis 14 preferably comprises a front portion 56, a rear portion 58, a crotch portion 57. The chassis 14 preferably further comprises elasticized leg cuffs 32, an elasticized waistband 34, elasticized side panels 30 and longitudinal side regions 88. The longitudinal side regions 88 preferably comprise a polymeric material to facilitate the seaming process which is described in greater detail below.

The training pants 20 preferably further comprises an absorbent assembly 22 preferably secured to the chassis 14 by any means known in the art. The absorbent assembly preferably comprises a liquid permeable topsheet 24, a liquid impervious backsheet 26 and an absorbent core 28 sandwiched between the topsheet 24 and the backsheet 26.

Figure 2:
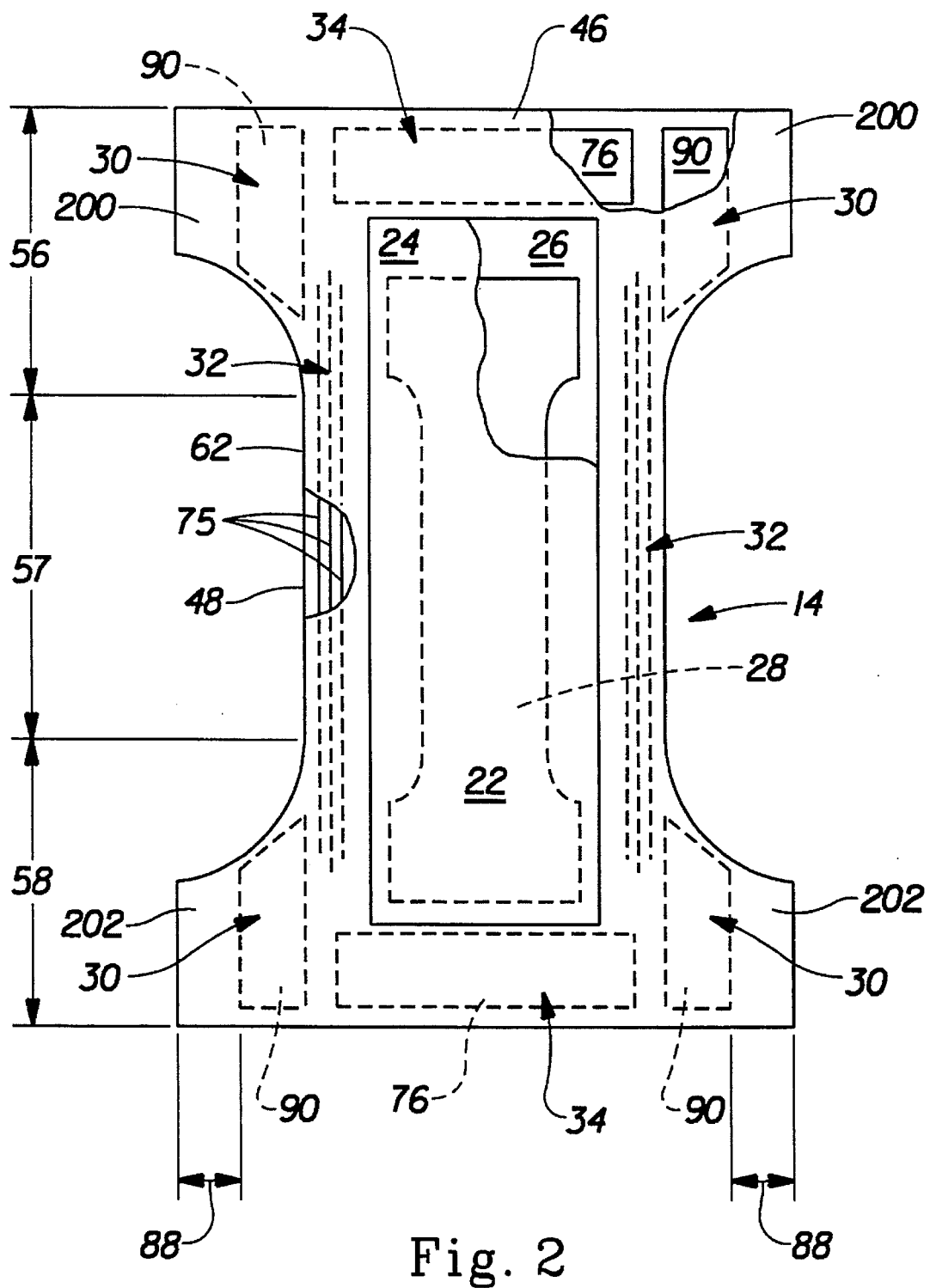
FIG. 2 is a plan view of the chassis of the training pant of FIG. 1 having portions cut away to reveal the underlying structure, the surface which will form the outer surface of the disposable article facing away from the viewer.

FIG. 2 is a partially cut-away perspective view of the disposable article 20 of FIG. 1, prior to the front portion 56 and the rear portion 58 of the chassis 14 being joined together. (As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element.) As shown in FIG. 2, a preferred embodiment of the chassis 14 will comprise an outer cover 48, an inner cover 46, elastic side panel members 90, elastic waistband members 76, and elastic strands 75 secured between the inner cover 46 and the outer covers 48.

The inner cover 46 is that portion of the chassis 14 which will form the interior of the disposable training pants 20. The outer cover 48 is that portion of the chassis 14 which will form the exterior of the disposable training pants 20, i.e. face away from the wearer. The outer cover 48 is preferably liquid impervious or hydrophobic, yet breathable or pervious to vapors. The inner cover 46 and the outer cover 48 are preferably compliant, soft feeling, and non-irritating to the wearer's skin. A suitable inner or outer cover may be manufactured from a wide range of materials, such as plastic films; or woven or non-woven webs of natural fibers (e.g. wood or cotton fibers), synthetic fibers (e.g. polyester or polypropylene fibers), or a combination of natural and synthetic fibers. Preferably, the inner and outer covers 46 and 48 comprise a significant amount of thermoplastic fibers, typically 50% or more, preferably 100%. Material suitable for use as an inner or outer cover is Series 6700 Nonwoven manufactured by Scott Nonwovens of Landisville, N.J.

In a preferred embodiment of the present invention, at least a portion of the inner and outer covers 46, 48 will be subjected to mechanical stretching in order to provide a "zero strain" stretch laminate that forms the elasticized side panels 30. Thus, the inner and outer covers 46, 48 are preferably elongatable, most preferably drawable, but not necessarily elastomeric, so that the inner and outer covers 46, 48 will, upon mechanical stretching, be at least to a degree permanently elongated such that they will not fully return to their original undistorted configuration. In preferred embodiments, the inner and outer covers 46, 48 can be subjected to mechanical stretching without undue rupturing or tearing. Thus, it is preferred that the inner and outer covers 46, have a low cross-machine direction (lateral direction) yield strength.

Suitable "zero strain" stretch laminates and methods for producing them are disclosed in U.S. Pat. No. 5,330,458 entitled "Absorbent Article With Elastic Feature Having A Portion Mechanically Prestrained" issued to Buell et al., on Jul. 19, 1994; U.S. Pat. No. 2,075,189 issued to Galligan on Mar. 30, 1937; U.S. Pat. No. 3,025,199 issued to Harwood on Mar. 13, 1962; U.S. Pat. Nos. 4,107,364 and 4,209,563 issued to Sisson on Aug. 15, 1978 and Jun. 24, 1980, respectively; U.S. Pat. No. 4,834,741 issued to Sabee on May 30, 1989; and U.S. Pat. No. 5,151,092 issued to Buell et al., on Sep. 29, 1992. All of the above referenced patents are hereby incorporated by reference.

Alternatively, the inner and outer covers 46, 48 or portions thereof may comprise a structural elastic-like film (SELF) web. A structural elastic-like film web is an extensible material that exhibits an elastic-like behavior in the direction of elongation without the use of added elastic materials. SELF webs suitable for the present invention are more completely described in the co-pending, commonly assigned U.S. patent application Ser. No. 08/203,456 entitled "Absorbent Article with Multiple Zone Structural Elastic-Like Film Web Extensible Waist Feature" filed by Donald C. Roe, et al. on Feb. 24, 1994, and International Application WO 9503765, entitled "Web Materials Exhibiting Elastic-Like Behavior" published Feb. 9, 1995, in the names of Chappell et al., both of which are incorporated herein by reference.

A more detailed description of a suitable training pant, as well as preferred components and alternative embodiments, in which the method and seams of the present invention may be used can be found in U.S. Pat. No. 5,236,430 entitled "Disposable Training Pant Having Fusion-Slit Side Seams", issued to Russell P. Bridges on Aug. 17, 1993, and U.S. Pat. No. 5,246,433 entitled "Elasticized Disposable Training Pant and Method of Making the Same", issued to Hasse et al. on Sep. 21, 1993. The specification, claims and drawings of each of these patents are hereby incorporated by reference herein.

Method of Making a Flangeless Seam

Figure 3:
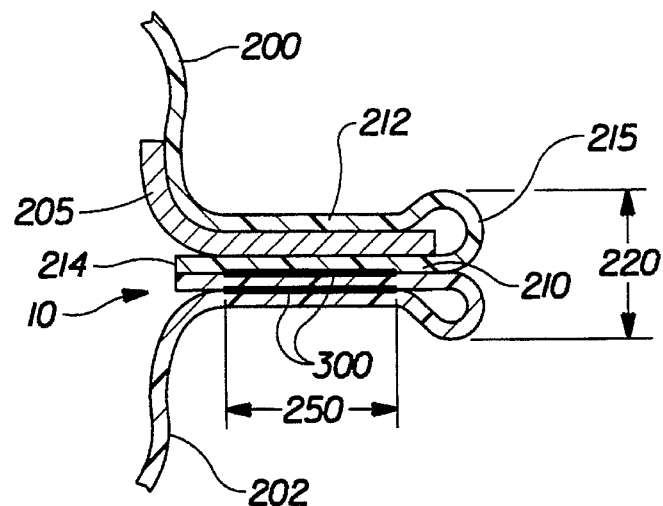
FIG. 3 is an enlarged cross-sectional view of one embodiment of a seam made by one embodiment of the present invention in the configuration in which portions of the seam are joined together.

One preferred method for making flangeless seams especially useful in disposable articles, such as training pants, incontinence articles and the like is shown schematically in FIGS. 9A–9G. The step depicted in FIG. 9A shows providing a web 400 having longitudinal side edges 410 that will be processed into disposable article 15 having first members 200 and second members 202 to be joined. FIG. 9B shows barrier member 205 provided juxtaposed at least a portion of each longitudinal side edge 410. FIG. 9C shows the longitudinal side edges 410 being folded over the web 400. FIG. 9D shows the chassis 14 of the disposable article 15 with the side notches 10 removed. First member 200 is preferably folded about the barrier member 205 providing opposing proximal and distal portions 210 and 212. The barrier member 205 is preferably disposed at least partially between the opposing proximal and distal portions 210 and 212. (The "proximal portion" 210 is that portion of the first member 200 which is joined, or will be joined, either directly or indirectly, to a portion of the disposable article 15, preferably other than the second member 202. The "distal portion" 212 is that portion of the first member 200 comprising the free end 214 which is generally not joined to any portion of the disposable article other than the second member 202.) FIG. 9E shows the second member 202 of the disposable article 15 being provided juxtaposed at least a portion of the first member 200 forming a laminate 220 of the first member 200, the second member 202 and the barrier member 205. (A more detailed drawing of the laminate 220 is shown in FIG. 3) FIG. 9F shows a joining means 300 being applied across at least a portion of laminate 220, the joining means 300 joining at least a portion of the first member 200 and the second member 202 to form a seam 10. The barrier member 205 prevents the joining means 300 from joining the opposing proximal and distal portions 210 and 212. Thus, the seam 10 may be opened from the configuration in which it is sealed (one embodiment is shown in FIG. 3) to a flangeless configuration wherein opposing proximal and distal portions 210 and 212 of the first member 200 are in a relatively planar configuration with regard to one another (An example of the seam in a planar configuration is shown in FIG. 9G and in more detail in FIG. 3A).

It should be noted that the scope of the present invention is not intended to be limited by the particular order in which the steps of the method are described. For example, although the side notches 10 are shown to be removed first in FIG. 9D, it is contemplated that the side notches 10 may be removed before, after or during any other step of the process. Further, the method of the present invention can be performed on-line in conjunction with, or at separate time and/or in a location remote from, the manufacture of the absorbent article which comprise the seams formed by the present method. If the process is performed on-line in conjunction with the manufacture of the absorbent article, the seams may be formed before, after or at the same time that the first and second members 200 and 202 are joined with the chassis 14 of the disposable article 15. Also, it should be understood that the exact size and shape of any member comprised in the disposable article 15, as well as the materials comprised in the members may vary depending on the desired characteristics of the disposable article 15.

The method for manufacturing a flangeless seam preferably includes providing a first member 200. The chassis 14 preferably comprises at least one longitudinal side region 88 having a first member 200 and a second member 202. As shown in FIG. 2, the chassis 14 more preferably comprises a pair of opposing longitudinal side regions 88, each of which comprise a first member 200 and a second member 202. (Although the first members 200 are shown in FIG. 2 to be disposed in the front portion 56 and the second members 202 are shown to be disposed in the rear portion 58, embodiments are contemplated wherein the first members 200 are disposed in the rear portion 58 and the second members 202 are disposed in the front portion 56.)

The first and second members 200 and 202 may be separate members joined to the longitudinal side regions 88 or may be integral with the longitudinal side regions 88. (As used herein, the term "integral" refers to elements that are joined to one another in such a way that the elements are neither divided nor discontinuous with the other elements.) If the first and second members 200 and 202 are joined with the chassis 14, any suitable means for joining known in the art may be used. In a preferred embodiments, the first and second members 200 and 202 are extensions of the topsheet 24, the backsheet 26, both the topsheet 24 and the backsheet 26 or any other element of the disposable article that may be suitable for joining to form a seam 10.

The first member 200 and the second member 202 may comprise any material known in the art that is suitable for use in disposable articles such as training pants 20 which may be joined together to form seam 10. Examples of suitable materials include, but are not limited to polymeric films, woven webs, nonwoven webs or combinations of these or other suitable materials known in the art. Examples of preferred materials include the carded nonwoven DPN290 available from Fiberweb, Clopay 1401 polyethylene film available from the Clopay Corporation of Cincinnati, Ohio, and FS2 or Plus polyethylene films available from Tredegar Film Products, Inc., of Terre Haute Ind.

The method of the present invention further comprises the step of providing a barrier member 205, as shown in FIGS. 3–7. The barrier member 205 is provided to ensure that when the seam 10 is formed, joining the first member 200 and the second member 202, at least a portion of the first member 200 is not joined with at least a portion of the second member 202. The barrier member 205 may take on any shape, size or configuration suitable for the particular seam to be formed. The barrier member 205 may comprise a single layer or any number of layers. (The multi-layer configurations may comprise a single barrier member folded upon itself any number of times or may comprise layers of unjoined material) The barrier member 205 may comprise any known material or means that will prevent the first member 200 and the second member 202 from becoming fully joined when the seam is formed. Further, the barrier member 205 may be a separate element joined to the first member or a separate member not joined to the first member 200, but merely provided in a position to act as a barrier while the seam is being formed. Alternatively, the barrier member 205 may comprise an element or material that is unitary or integrated with at least a portion of the first member 200, such as a material coextruded with the first member 200, or portion of the first member that has been chemically, mechanically or otherwise manipulated to act as a barrier to the joining means 300 used to form the seam.

Examples of suitable barrier members include, but are not limited to KEVLAR, NYLON, polypropylene films, polyethylene films, scrims, woven materials or laminates of any of these or any other suitable materials known in the art. Other suitable barrier member materials may comprise silicone, talc, clay, TEFLON, lotions or any other suitable release means that will prevent predetermined portions of the barrier member 205 from becoming joined when the joining means 300 is applied. Yet other suitable barrier members comprise foams; laminates of films, foams and/or nonwoven webs; adhesives; coated or non-coated paper products; cotton and cotton-flocked films. Generally, the composition of the barrier member 205 will be limited only by the particular joining means 300 which will be used and the strength characteristics necessary to provide an acceptable seam.

The means by which the barrier member 205 may be provided, as well the timing and location for providing the barrier member 205 will be dependent on the exact barrier member 205 chosen. However, once a particular barrier member 205 has been chosen, the barrier member 205 may be provided by any suitable means known in the art. For instance, if a barrier member 205 comprising silicone is chosen, one preferred means for providing the barrier member 205 is spraying the silicone composition onto at least a portion of the first member 200.

Figure 4:
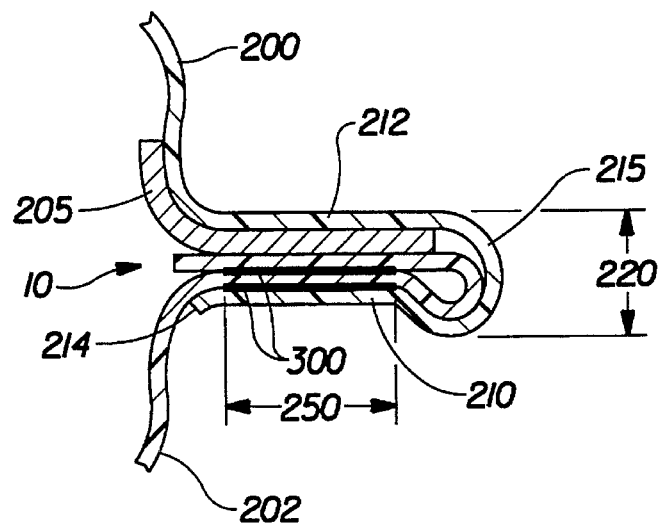
FIG. 4 is an enlarged cross-sectional view of one embodiment of a seam made by one embodiment of the present invention in the configuration in which portions of the seam are joined together.

In one preferred embodiment, as shown in FIG. 3, once the barrier member 205 is provided, the first member 200 is folded about the barrier member 205. (As stated above, the exact order of the steps of the process are not critical, thus, the barrier member 205 may be provided before or after the first member 200 is folded.) The fold 215 preferably separates the first member 200 into two portions, a proximal portion 210 and an opposing distal portion 212. Preferably, the barrier member 205 is disposed at least partially between the opposing proximal and distal portions 210 and 212, as shown in FIG. 3. The length of the proximal portion 210 and the distal portion 212 is not critical, and either or both may comprise any number of layers and/or folds. In fact, it is recognized that one way to increase the strength of the finished seam is to provide more material in the seam area 250. This is especially relevant when the joining means 205 comprises some sort of heat, pressure, heat and pressure, or ultrasonic bonding wherein at least a portion of the bond comprises the material to which the bonding means is applied. In an alternative embodiment, the first member 200 is folded about the barrier member 205 and at least a portion of the second member 202, as shown in FIG. 4.

The method of the present invention further comprises the step of providing a second member 202. The second member 202 is preferably provided juxtaposed at least a portion of the distal portions 210 of the first member 200 at a location wherein the opposing proximal and distal portions 210 and 212 have the barrier member 205 disposed between them. This forms a laminate 220 (one embodiment of which is shown in FIG. 3) including the proximal and distal portions 210 and 212, and the barrier member 205. (As used herein, the term "laminate" refers to any number of materials that are in a generally overlapping configuration so as to form at least two layers. The materials included in the laminate may comprise single layer materials or laminates of similar or different materials. Further, any laminates comprised in the laminate 220 may have layers that are joined or unjoined with each other.)

Figure 3A:
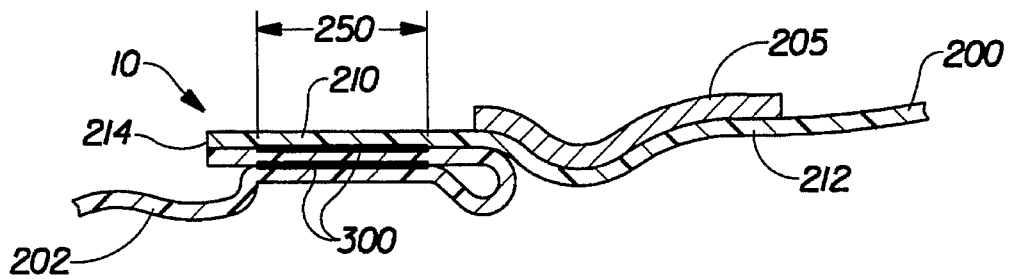
FIG. 3A is an enlarged cross-sectional view of the seam area shown in FIG. 3 in an open configuration.

Once the materials comprised in the laminate 220 have been properly configured, the seam 10 is formed. The seam 10 comprises those portions of the laminate 220 that are joined together (i.e. at least a portion of the first member 200 and at least a portion of the second member 202). To form the seam 10, a joining means 300 is applied across at least a portion of the laminate 220. In one preferred embodiment, the joining means 300 is applied across the seam are 250 as shown in FIG. 3. The joining means 300 joins at least a portion of the first member 200 and at least a portion of the second member 202. However, the barrier member 205 prevents the joining means 300 from joining at least a portion of the proximal portion 210 with the distal portion 212. Thus, a flangeless seam 10 is formed that may be "opened" to the relatively planar configuration shown in FIG. 3A. (As used herein, the terms "open" or "opened" refer to pulling apart or separating predetermined portions of the laminate 220, such as the proximal portion 210 and the distal portion 212, once the laminate has been seamed so as to form a relatively planar configuration, an example of which is shown in FIG. 3A.)

The joining means 300 may comprise any means suitable for joining the materials comprised in the first and second members 200 and 202. However, a joining means must be chosen that will join the desired portion or portions of the first member 200 with the desired portion or portions of the second member 202 while not joining to those portions of the first member 200 and the second member 202 which have been designated to remain unjoined. Thus, it is important to choose a joining means 300 that will work effectively with the barrier member 205 to achieve the desired results. Suitable joining means include, but are not limited to, adhesives, pressure bonding means, heat bonding means, heat and pressure bonding means, ultrasound bonding means, infrared bonding means or any other joining means or combination of joining means known in the art.

Examples of suitable adhesive joining means include, but are not limited to, hot melt adhesives such as Findley 2120, or Findley 2379 available from Findley Adhesives Corporation of Wauwatosa, Wis. Such adhesive may be applied with slot, spiral or control spray coating equipment such as those available from Nordson Corporation of Norcross, Ga. Examples of methods and apparatus for treating materials with ultrasonic energy are disclosed in U.S. Pat. No. 3,657,033 issued to Sager on Apr. 18, 1972 entitled "Method and Apparatus for Continuous Cutting and Joining of Thermoplastic Sheet Material"; U.S. Pat. No. 4,400,227 issued to Riemersma on Aug. 23, 1983; U.S. Pat. No. 4,430,148 issued to Schaefer on Feb. 7, 1984; U.S. Pat. No. 4,560,427 issued to Flood on Dec. 24, 1985 entitled "Ultrasonic Seal and Cut Method and Apparatus"; and U.S. Pat. No. 4,693,771 issued to Payet, et al. on Sep. 15, 1987 entitled "Woven Textile Fabric Having and Ultrasonically Cut and Sealed Edge and Apparatus and Process for Producing Same"; all of which references are incorporated herein by reference. U.S. Pat. No. 5,236,430 entitled "Disposable Training Pant Having Fusion-Slit Seam", issued to Russell Bridges on Aug. 17, 1993; and U.S. Pat. No. 3,457,132 issued to Tuma, et al. on Jul. 22, 1969 entitled "Apparatus for Severing and Sealing Webs of Heat Sealable Packaging Material in a Single Operation", disclose preferred methods and apparatus for severing and sealing webs using thermal energy and mechanical energy including ultrasound. These references are also incorporated herein by reference.

Figure 5:
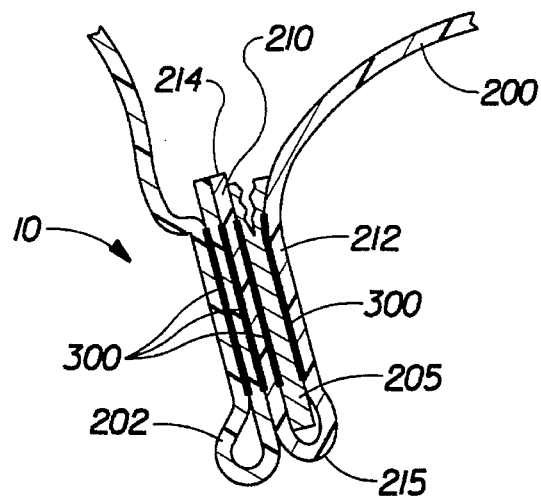
FIG. 5 is an enlarged cross-sectional view of an alternative embodiment of a seam in the configuration in which portions of the seam are joined together.
Figure 6:
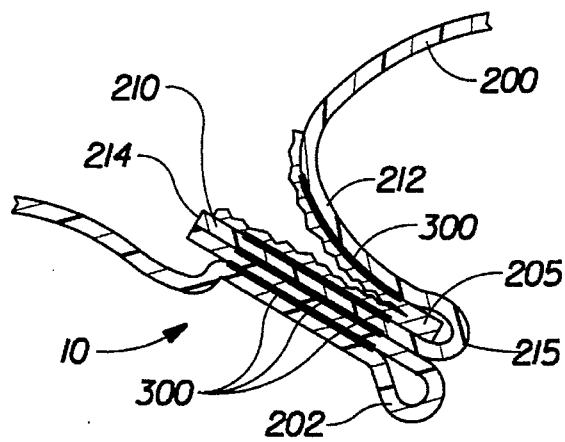
FIG. 6 is an enlarged cross-sectional view of the seam area shown in FIG. 5 in a partially open configuration.
Figure 7:
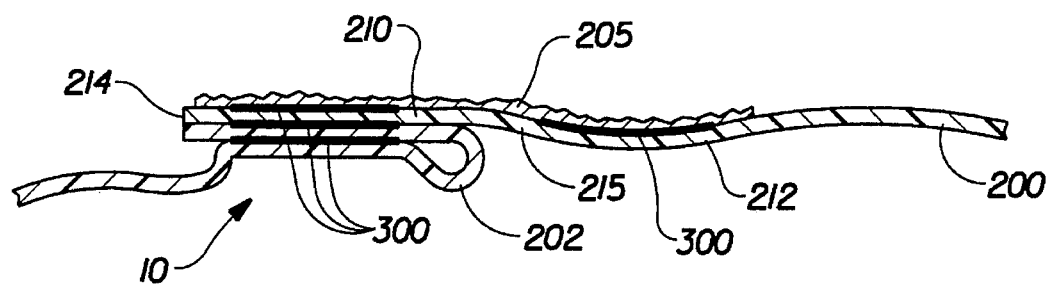
FIG. 7 is an enlarged cross-sectional view of the seam area shown in FIG. 5 in an open configuration.

An alternative embodiment of a seam produced by the method of the present invention is shown in FIGS. 5–7. FIG. 5 shows the first and second members 200 and 202 of the present invention in a configuration after the first and second members 200 and 202 have been provided juxtaposed one another, the barrier member 205 has been provided, the first member 200 has been folded about the barrier member 205 and the joining means has been applied, as described above. In this embodiment, joining means 205 preferably joins not only the proximal portion 210 of the first member 200 with at least a portion of the second member, but also joins the barrier member 205 to both the proximal portion 210 and the distal portion 212 of the first member 200. Thus, as shown in FIGS. 5–7, to open the flangeless seam 10, the barrier member 205 is preferably torn or separated. (An example of this seam configuration is shown in FIG. 7.) Although the structure of barrier member 205 itself is shown to be tearing or separating, the barrier member 205 could alternatively separate from either or both the proximal portion 210 or the distal portion 212. Therefore, seams with different opening characteristics can be produced by the method of the present invention depending on the structural characteristics of the barrier member 205 or the joining means 300 chosen.

In one particularly preferred embodiment, the barrier member 205 comprises a nonwoven material that will tear with less force than is needed to separate the barrier member 205 from either the proximal portion 210 or the distal portion 212. Thus, a nonwoven material will be disposed along at least a portion of one surface of both the proximal portion 210 and the distal portion 212 of the first member 200. This configuration is especially preferred when the seam 10 is to be used in a disposable article such as the one shown in FIG. 8. The torn barrier member 205 provides a skin friendly surface that can be disposed against the skin of a wearer once the seam 10 is opened as is shown in FIG. 7.

Figure 8:
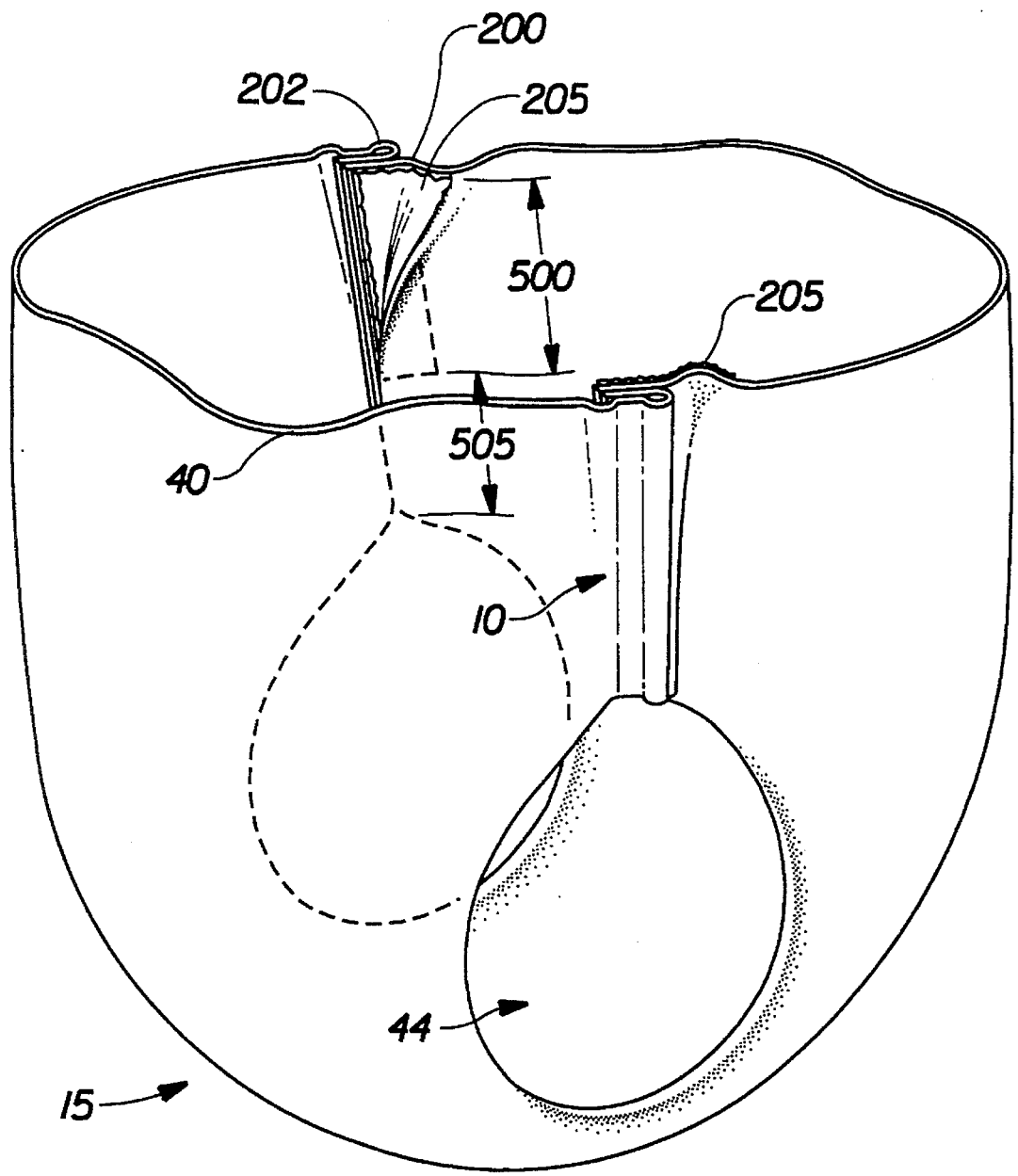
FIG. 8 is a perspective view of one preferred disposable article comprising the openable seams shown in FIGS. 5–7.

FIG. 8 shows one preferred embodiment of a disposable garment 15 comprising of the seam 10 formed by one method of the present invention. The seam 10 as shown in FIG. 8 is preferably formed by the method described above wherein the barrier member 205 is tearable or separable, and preferably comprises a skin friendly material. The barrier member 205 may span the entire length of the seam 10 or any portion of the seam 10. Thus, a seam 10 may be formed having an "openable portion" 500 and a "closed portion" 505. (As used herein, the term "openable portion" refers to that portion of the seam comprising a barrier member allowing the seam to be opened to a flangeless configuration. The term "closed portion" refers to that portion of a seam that has no barrier member, and thus may not be opened.) As shown in FIG. 8, the openable portion 500 of the seam 10 may be shorter in length than the distance between the waist hoop 40 and the leg openings 44. This may give the user a greater fit range for a given size garment or may be used to help the user to tailor the fit of the garment to the particular wearer by allowing the user to open the seam 10 when desired to provide a particular size or fit.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making a flangeless seam by joining two members of a disposable article, the method comprising the steps of:

providing a first member of the disposable article;

providing a barrier member;

folding the first member of the disposable article about the barrier member providing opposing proximal and distal portions of the first member, the barrier member being disposed at least partially between the opposing proximal and distal portions;

providing a second member of the disposable article in a folded configuration juxtaposed at least a portion of the first member to form a laminate including the first member, the second member and form barrier member; and applying a joining means across at least a portion of the laminate joining at least a portion of the first member and the second member, the barrier member preventing the joining means from joining the proximal portion with the distal portion.

2. The method of claim 1 further comprising the step of pulling apart the first member and the second member to form a flangeless seam.

3. The method of claim 1 further comprising the step of removing the barrier member after the joining means is applied.

4. The method of claim 1 wherein the step of folding the first member includes folding the first member before the barrier in interposed between the opposing proximal and distal portions.

5. The method of claim 1 wherein the first member includes more than one fold.

6. The method of claim 1 wherein the barrier member is separably joined to the proximal portion such that the proximal portion can be pulled apart from the barrier member to form a flangeless seam.

7. The method of claim 1 wherein the barrier member is separably joined to the distal portion such that the distal portion can be pulled apart from the barrier member to form a flangeless seam.

8. The method of claim 1 wherein the barrier member is separably joined to both the proximal portion and the distal portion such that the proximal and distal portions can be pulled apart from the barrier member to form a flangeless seam.

9. A method of making a flangeless seam by joining two members of a disposable article, the method comprising the steps of:

providing a first member of the disposable article;

providing a barrier member;

folding the first member of the disposable article about the barrier member providing opposing proximal and distal portions of the first member, the barrier member being disposed at least partially between the opposing proximal and distal portions;

joining the barrier member to both the proximal and the distal portions;

providing a second member of the disposable article juxtoposed at least a portion of the first member to form a laminate including the first member, the second member and the barrier member; and applying a joining means across at least a portion of the laminate joining at least a portion of the first member and the second member, the barrier member preventing the joining means from joining the proximal portion with the distal portion.

10. The method of claim 9 wherein the barrier member comprises a separable material.

11. The method of claim 10 further comprising the step of separating at least a portion of the separable material to form a flangeless seam where the separable material has been separated.

12. The method of claim 1 wherein the barrier member is a separate member from the second member.

13. The method of claim 1 wherein the barrier member is integral with at least a portion of the second member.

14. The method of claim 1 wherein the first member is folded about both the barrier member and at least a portion of the second member.

15. The method of claim 1 wherein the joining means consists any of the bonding means selected from the following group: pressure sensitive adhesive bonding, hot melt adhesive bonding, heat bonding, pressure bonding, heat and pressure bonding, ultrasonic bonding, and infrared bonding.

16. The method of claim 1 wherein the barrier member comprises a nonwoven.

17. The method of claim 1 wherein the barrier member comprises a film.

18. The method of claim 1 wherein the barrier member comprises a laminate of a nonwoven and a film.

19. A method of making a flangeless seam by joining two members of a disposable article, the method comprising the steps of:

providing a first member of the disposable article;

providing a barrier member;

folding the first member of the disposable article about the barrier member providing opposing proximal and distal portions of the first member, the barrier member being disposed at least partially between the opposing proximal and distal portions;

providing a second member of the disposable article in a folded configuration juxtaposed at least a portion of the first member to form a laminate including the first member, the second member and the barrier member;

providing a joining means across at least a portion of the laminate joining at least a portion of the first member and the second member, the barrier member preventing the joining means from joining the proximal portion with the distal portion;

removing the barrier means; and pulling apart the first member and the second member to form a flangeless seam.

* * * * *